United States Patent
Artsyukhovich et al.

(10) Patent No.: US 10,299,671 B2
(45) Date of Patent: *May 28, 2019

(54) INTEGRATED OCT-REFRACTOMETER SYSTEM FOR OCULAR BIOMETRY

(71) Applicant: NOVARTIS AG, Basel (CH)

(72) Inventors: Alexander N. Artsyukhovich, San Juan Capistrano, CA (US); Z. Aras Aslan, Foothill Ranch, CA (US); Lingfeng Yu, Rancho Santa Margarita, CA (US); Mikhail Boukhny, Laguna Niguel, CA (US)

(73) Assignee: Novartis AG, Basel (CH)

( * ) Notice: Subject to any disclaimer, the term of this patent is extended or adjusted under 35 U.S.C. 154(b) by 253 days.

This patent is subject to a terminal disclaimer.

(21) Appl. No.: 15/370,866

(22) Filed: Dec. 6, 2016

(65) Prior Publication Data

US 2017/0079522 A1 Mar. 23, 2017

Related U.S. Application Data

(63) Continuation of application No. 14/031,799, filed on Sep. 19, 2013, now Pat. No. 9,538,911.

(51) Int. Cl.
*A61B 3/00* (2006.01)
*A61B 3/103* (2006.01)
(Continued)

(52) U.S. Cl.
CPC .......... *A61B 3/0025* (2013.01); *A61B 3/0041* (2013.01); *A61B 3/102* (2013.01);
(Continued)

(58) Field of Classification Search
CPC ......... A61B 3/102; A61B 3/1225; A61B 3/14; A61B 3/185; A61B 3/0058; A61B 3/1208;
(Continued)

(56) References Cited

U.S. PATENT DOCUMENTS 7,699,468 B2 4/2010 Gaida
7,703,913 B2 * 4/2010 Huang ..................... G02C 5/10
351/110

(Continued)

FOREIGN PATENT DOCUMENTS

CN 203089533 U 7/2013
DE 102011113953 A1 3/2013
(Continued)

OTHER PUBLICATIONS

Ophthalmic examination Handbook, Jun. 1, 2005, 4th Edition, pp. 52-53.

(Continued)

*Primary Examiner* — Collin X Beatty
*Assistant Examiner* — Grant A Gagnon

(57) ABSTRACT

A Slit-lamp-or-Microscope-Integrated-OCT-Refractometer system includes an eye-visualization system, configured to provide a visual image of an imaged region in an eye; an Optical Coherence Tomographic (OCT) imaging system, configured to generate an OCT image of the imaged region; a refractometer, configured to generate a refractive mapping of the imaged region; and an analyzer, configured to determine refractive characteristics of the eye based on the OCT image and the refractive mapping, wherein the refractometer and the OCT imaging system are integrated into the eye visualization system.

28 Claims, 9 Drawing Sheets

(51) Int. Cl.
  *A61B 3/135* (2006.01)
  *A61B 3/10* (2006.01)
  *A61F 9/008* (2006.01)

(52) U.S. Cl.
  CPC ............ *A61B 3/103* (2013.01); *A61B 3/1015* (2013.01); *A61B 3/135* (2013.01); *A61F 2009/00851* (2013.01); *A61F 2009/00887* (2013.01); *A61F 2240/002* (2013.01)

(58) Field of Classification Search
  CPC ..... A61B 3/0025; A61B 3/0041; A61B 3/103; A64B 3/12
  USPC ........................................................ 351/206
  See application file for complete search history.

(56) References Cited

U.S. PATENT DOCUMENTS

| | | | |
|---|---|---|---|
| 7,708,406 B2* | 5/2010 | Koest | A61B 3/103 351/206 |
| 8,049,873 B2 | 11/2011 | Hauger et al. | |
| 2003/0007124 A1* | 1/2003 | Levine | A61F 9/008 351/206 |
| 2008/0287929 A1* | 11/2008 | Holliday | A61F 9/00806 606/10 |
| 2009/0033871 A1* | 2/2009 | Chavez-Pirson | H01S 3/06754 351/206 |
| 2010/0134760 A1* | 6/2010 | Salvati | A61B 3/0025 351/206 |
| 2010/0191230 A1* | 7/2010 | Dick | A61B 3/1005 606/5 |
| 2010/0271594 A1* | 10/2010 | Bergner | A61B 3/0025 351/206 |
| 2011/0228223 A1* | 9/2011 | Jiao | A61B 3/102 351/206 |
| 2013/0258283 A1* | 10/2013 | Goto | A61B 3/14 351/206 |
| 2013/0286347 A1* | 10/2013 | Teijido | A61B 3/0083 351/206 |
| 2014/0300863 A1* | 10/2014 | Fukuma | A61B 3/12 351/206 |
| 2014/0327884 A1 | 11/2014 | Buhren et al. | |
| 2015/0085252 A1* | 3/2015 | Fujimura | A61B 3/15 351/208 |

FOREIGN PATENT DOCUMENTS

| | | |
|---|---|---|
| JP | 2006-516447 A | 7/2006 |
| JP | 2009-517092 A | 4/2009 |
| JP | 2009-230141 A | 10/2009 |
| RU | 2448339 C1 | 4/2012 |
| WO | 2004/071270 A2 | 8/2004 |
| WO | 2009/136659 A1 | 11/2009 |
| WO | 2013/097885 | 7/2013 |

OTHER PUBLICATIONS

M. L. Gabriele et al., "Optical Coherence Tomography: History, Current Status, and Laboratory Work", Investigative Ophthalmology & Visual Science, 52(5), Apr. 14, 2011, pp. 2425-2436.

* cited by examiner

INTEGRATED OCT-REFRACTOMETER SYSTEM FOR OCULAR BIOMETRY

BACKGROUND

Technical Field

Embodiments disclosed herein are related to Integrated-OCT-Refractometer systems. In more detail, embodiments are related to eye-visualization systems, Optical Coherence Tomographic (OCT) imaging systems, and refractometers to determine refractive characteristics of the eye based on the OCT image and a refractive mapping.

Related Art

Current ophthalmic refractive surgical methods, such as cataract surgery, intra-corneal inlays, Laser-Assisted in situ Keratomileusis (LASIK), and photorefractive keratectomy (PRK), rely on ocular biometry data to prescribe the best refractive correction. Historically, ophthalmic surgical procedures used ultrasonic biometry instruments to image portions of the eye. In some cases these biometric instruments generated an A-scan of the eye: an acoustic echo signal from all interfaces along an imaging axis that was typically aligned with an optical axis of the eye: either parallel with it, or making only a small angle. Other instruments generated B-scan, essentially assembling a collection of A-scans, taken successively as a head or tip of the biometry instrument was scanned along a scanning line. This scanning line was typically lateral to the optical axis of the eye. These ultrasonic A- or B-scans were then used to measure and determine biometry data, such as an ocular Axial Length, an Anterior Depth of the eye, or the radii of corneal curvature. Examples of such ultrasonic ocular biometry devices include the Alcon UltraScan and Alcon OcuScan RxP.

In some surgical procedures a second, separate keratometer was used to measure refractive properties and data of the cornea. The ultrasonic measurements and the refractive data were then combined in a semi-empirical formula to calculate the characteristics of the optimal Intra Ocular Lens (IOL) to be prescribed and inserted during the subsequent cataract phaco surgery.

More recently, the ultrasonic biometry devices have been rapidly giving way to optical imaging and biometry instruments that are built on the principle of Optical Coherence Tomography (OCT). Examples include the Zeiss IOL Master and the Haag-Streit Lenstar. Such OCT instruments are now used in 80-90% of all IOL prescription cases. Among others, their success is due to the non-contact nature of the imaging and to the higher precision than that of the ultrasound biometers.

Even with these recent advances, however, substantial further growth and development is needed for the functionalities of the biometric and imaging instruments.

SUMMARY

1. One of the problems with the present instruments is that the methods that are used to determine biometrical information heavily rely on assumptions going into the used eye-models, such as the speed of ultrasound in the various ocular media and the refractive indices of various ocular media. They are also based on a simplified representation of the human eye, such as the assumption that the refractive index and the ultrasound speed do not vary with intra-ocular location and time, whereas in reality they do. Accordingly, a system that models the eye with measured eye-parameters instead of using assumptions would provide better accuracy.

2. Further, the applied models use average values, averaged over refractive results from many surgeries and large patient populations. As such, the present methods are based on averaged information and neglect or underestimate patient-to-patient variations. These variations can include variations with age, gender, region, and other factors. A system that can capture patient-to-patient variations would improve the surgical choices.

3. The ocular biometry measurements are typically performed weeks prior to cataract surgery, in a medical or ophthalmic office. However, there can be non-negligible changes in the biometry of the patient's eye in the weeks leading up to the surgery. These changes can be compounded by the preparation for the surgery itself, such as the administering of relaxants and other pharmaceuticals, as well as the differences between the surgical theater and the medical office. Thus, a system that can provide biometric information closer to the time of surgery would be helpful.

4. Moreover, since the biometrical measurements are performed on a cataractous eye, the optical signals are often blurred or distorted to some degree. Hence the prescription based on the eye-modeling sometimes deviates from the optimal prescription. Hence, a system that provides biometric information based on un-blurred measurements provides enhanced precision.

5. Since in present procedures separate biometrical and imaging instruments are used, the biometrical and imaging data needs to be cross-referenced and registered, which raises additional challenges. A system that has integrated measurement capability can provide a better registration.

6. Beyond all the above problems of the preparatory biometry and imaging that can deliver sub-optimal results for a particular eye of a particular patient at a particular time, an additional problem is that biometry is not available during the surgery, even though it could provide useful additional feedback and control information for the surgeon. The first example is the stage when the relaxing incisions have been performed based on pre-operative biometry, but the IOL has not been inserted yet. At this point, a system that can carry out additional measurements to check whether having performed the prescribed incisions indeed achieved the refractive results predicted by the pre-operational modeling could be useful to provide additional corrections or adjustments.

7. Another utility of the intra-operative biometry can be that when a toric IOL is inserted into an astigmatic eye, the axis of the toric IOL should be optimally oriented relative to the astigmatism of the eye. Presently, the surgeon is guided by the prescription based on the pre-operative biometry. However, it can be helpful to track the orientation of the axis of the toric IOL by intra-operative biometry to ensure that the IOL axis is indeed oriented by the surgeon as prescribed. Furthermore, such a system could perform an additional intra-operative biometry to check whether the pre-operative prescription for the orientation angle remains indeed optimal. The result of this biometry can be relayed to the surgeon in a heads-up display inside the surgical microscope to guide the orientation of the toric axis efficiently.

8. In a similar vein, the centration of the IOL during cataract surgery is important as well. Again, an intra-operative biometry system can provide very useful guidance for the surgeon who carries out the IOL insertion.

At least for these reasons 1-8, the need exists for instruments and methods that deliver integrated imaging and biometric information related to an individual eye of an individual patient at a time suitable for making and adjusting step of the cataract surgery, IOL selection and insertion.

Remarkably, in spite of these needed functionalities, the integration of the refractive and imaging instruments is in its infancy. In particular, presently no intra-operative microscope is available with a refractive biometric device and an OCT imaging system integrated into it.

To address the above needs, embodiments of the present invention include a Slit-lamp-or-Microscope-Integrated-OCT-Refractometer system comprising an eye-visualization system, configured to provide a visual image of an imaged region in an eye; an Optical Coherence Tomographic (OCT) imaging system, configured to generate an OCT image of the imaged region; a refractometer, configured to generate a refractive mapping of the imaged region; and an analyzer, configured to determine refractive characteristics of the eye based on the OCT image and the refractive mapping, wherein the refractometer and the OCT imaging system are integrated into the eye visualization system.

Some embodiments include an intra-operative biometer, comprising: a surgical microscope, configured to provide a visual image of an imaged region in an eye; an Optical Coherence Tomographic (OCT) imaging system, configured to generate an OCT image of the imaged region; a refractometer, configured to determine refractive information of the imaged region; an analyzer, configured to determine biometric information of the eye based on the OCT image and the refractive information; and a heads-up display, configured to display the determined biometric information in an optical pathway of the surgical microscope.

Some embodiments include a method of operating an integrated OCT-refractometer system, the method comprising: generating an OCT image of an ophthalmic imaged region of an eye with an OCT imaging system; generating a refractive mapping of the ophthalmic imaged region with a refractometer; performing an integrated biometric analysis of the eye with an analyzer, based on the OCT image, the refractive mapping and an eye model; generating a biometric information with the analyzer based on the biometric analysis to inform a surgical choice; and displaying the biometric information via one of a video-display and a heads-up display.

Figure 1:
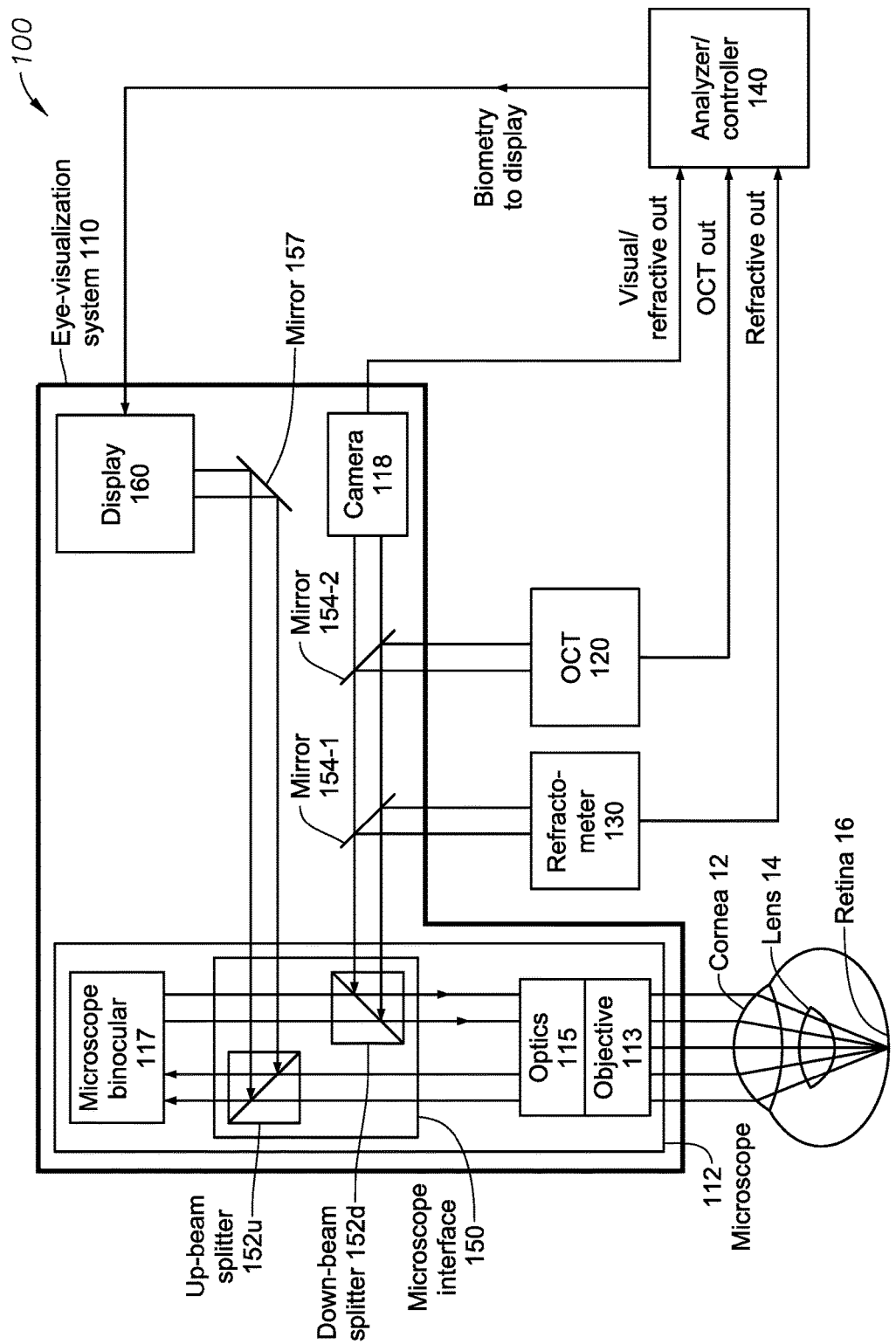
FIG. 1 is a diagram illustrating an embodiment of a Slit lamp-or-Microscope-Integrated-OCT-Refractometer System.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Embodiments of the present invention address the above outlined needs 1-8. In particular, instruments and methods according to the present invention include an Integrated-OCT-Refractometer System for ocular biometry that addresses those needs. Since this integrated system can be mounted on either a microscope or a slit lamp, it will be referred to as a Slit lamp-or-Microscope-Integrated-OCT-Refractometer System, or SMIORS. Slit-lamp-integrated systems can be useful for ophthalmic office-based systems where the surgical planning is performed. Microscope-integrated systems can be useful in an ophthalmic surgical theater. Embodiments of the SMIORS address the above needs as follows.

1. Embodiments of SMIORS can be configured to determine the refractive indices and characteristics and biometric information of the individual eyes of the individual patient. SMIORSs can be configured to utilize optical ray tracing software to build a custom eye biometry model.

Such a customized model can be used to prescribe cataract refractive surgery that provides customized refractive correction. Examples of optimizing the cataract surgery include planning out the type, location and orientation of the inserted IOLs, as well as planning the size, shape and placement of limbal relaxing incisions.

Moreover, if the eye of the patient exhibits, for example, a spatial variation of the refractive index, SMIORs can be capable of capturing this variation on some level and perform the biometric analysis accordingly.

2. In the same vein, embodiments of SMIORs can form a custom eye biometry model instead of using population-averaged values. In some other embodiments, SMIORSs can use a standard eye model, but with customized parameters. This is another aspect in which SMIORSs can deliver more precise surgical planning than the present population-averaged surgical planners.

3. Embodiments of SMIORSs can also be capable of determining the above biometric information very close to the time of the actual surgery, such as a surgical preparatory step. Accordingly, SMIORSs can avoid problems arising from the substantial time difference between the surgical planning office-visit and the subsequent cataract operation, and the change of the conditions between the two.

4. A SMIORS can perform biometrical measurements in the aphakic eye, i.e. after the cataractous lens has been removed. This allows the SMIORS to provide optical information that is not blurred by the cataract. Comparing the biometry of the aphakic eye with the pre-surgical modeling helps the surgeon to re-run the modeling simulations and modify the prescriptions as necessary.

5. Embodiments of SMIORSs can also be integrated: the OCT imaging system and the refractive system can be mounted on the same microscope instead of using the devices separately that would require subsequent registering and referencing. In the integrated SMIORSs, the refractive and OCT imaging information can be registered more reliably and precisely.

6. Some embodiments of SMIORs can be configured to perform biometry and refractive measurements intra-operatively. Such a SMIORS offers multiple advantages. For example, when the relaxing incisions have been performed in an early step of the cataract surgery, but the IOL has not been inserted yet, embodiments of the SMIORS can be used to perform a biometric measurement to check whether having performed the prescribed incisions indeed achieved the results predicted by the modeling. If not, the surgeon may wish to select an IOL that is different from the prescription based only on pre-operative biometry.

7. Another utility of the intra-operative biometry can be that when a toric IOL is inserted into an astigmatic eye, the axis of the toric IOL needs to be optimally oriented relative to the astigmatism. Presently, the surgeon is guided by the prescription of the pre-operative biometry. Clearly, it can be helpful to perform additional intra-operative biometry to check the orientation of the toric IOL as it is being inserted by the surgeon. Also, the intra-operative biometry can check whether the pre-operative prescription was indeed optimal. The result of this biometry can be relayed to the surgeon in a heads-up display inside the surgical microscope to guide the orientation of the toric axis efficiently.

8. Intra-operative biometry can also provide invaluable feedback for the surgeon as he or she attempts to center the IOL into the capsule. As before, providing the results of the intra-operative biometry in a heads-up display inside the surgical microscope can be particularly effective.

Some SMIORSs can address the just-described needs by getting mounted or integrated into a surgical microscope. Some embodiments can be capable of avoiding an invasion into the surgery space, in contrast to existing microscope-based OCT devices. For example, SWIORSs can be implemented into an existing port of the microscope. Since the demand for space in the design of a surgical microscope is particularly pressing, this can be a substantial advantage. Some SMIORS embodiments can be implemented by increasing the height of the microscope binoculars by less than 2 inches, or even by less than 1 inch.

Here it is mentioned that some existing systems managed to integrate a refractometer into a microscope. However, such systems provide only incomplete imaging information. Embodiments of the SMIORS offer a more complete imaging and biometry information by additionally integrating an OCT imaging system into the microscope or slit lamp as well.

FIG. 1 illustrates an embodiment of a Slit-lamp-or-Microscope-Integrated-OCT-Refractometer System, or SMIORS 100. The SMIORS 100 can include an eye-visualization system 110, configured to provide a visual image of an imaged region in an eye 10, an Optical Coherence Tomographic (OCT) imaging system 120, configured to generate an OCT image of the imaged region; a refractometer 130, configured to generate a refractive mapping of the imaged region; and an analyzer 140, configured to determine refractive characteristics of the eye based on the OCT image and the refractive mapping, wherein the OCT imaging system 120 and the refractometer 130 can be integrated into the eye visualization system 110.

The imaged region can be a portion or a region of the eye 10, such as a target of a surgical procedure. In a corneal procedure, the imaged region can be a portion of a cornea 12. In a cataract surgery, the imaged region can be a capsule and the (crystalline) lens 14 of the eye. The imaged region may also include the anterior chamber of the eye. In a retinal procedure, the imaged region can be a region of the retina 16. Any combination of the above imaged regions can be an imaged region as well.

The eye-visualization system 110 can include a microscope 112. In other embodiments, it can include a slit-lamp. The microscope 112 can be an optical microscope, a surgical microscope, a video-microscope, or a combination thereof. In the embodiment of FIG. 1, the eye-visualization system 110 (shown in thick solid line) can include the surgical microscope 112 that can include an objective 113, optics 115 and a binocular or ocular 117. The eye-visualization system 110 can also include a camera 118 of a video microscope.

The SMIORS 100 can further include the Optical Coherence Tomographic (OCT) imaging system 120. The OCT imaging system 120 can generate an OCT image of the imaged region. The OCT imaging system can be configured to generate an A-scan or a B-scan of the imaged region. The OCT image or image information can be outputted in an "OCT out" signal that can be used by the analyzer 140 in combination with an outputted "Refractive out" signal to determine biometric or refractive characteristics of the eye.

The OCT imaging system 120 can involve an OCT laser operating at a wavelength range of 500-2,000 nm, in some embodiments at a range of 900-1,400 nm. The OCT imaging system 120 can be a time-domain, a frequency-domain, a swept-frequency, or a Fourier Domain Mode Locking (FDML) OCT system 120.

Part of the OCT 120 can be integrated into the microscope, and part of it can be installed in a separate console. In some embodiments, the OCT portion integrated into the microscope can include only the OCT light source, such as the OCT laser. The OCT laser or imaging light, returned from the eye, can be fed into a fiber and driven to a second portion of the OCT 120, an OCT interferometer outside the microscope. The OCT interferometer can be located in a separate console, where suitable electronics is also located to process the OCT interferometric signals.

Embodiments of the OCT laser can have a coherence length that is longer than an extent of an anterior chamber of the eye, such as the distance between a corneal apex to a lens apex. This distance is approximately 6 mm in most patients, thus such embodiments can have a coherence length in the 4-10 mm range. Other embodiments can have a coherence length to cover an entire axial length of the eye, such as 30-50 mm. Yet others can have an intermediate coherence length, such as in the 10-30 mm range, finally some embodiments can have a coherence length longer than 50 mm. Some swept-frequency lasers are approaching these coherence length ranges. Some Fourier Domain Mode Locking (FDML) lasers are already capable of delivering a laser beam with a coherence length in these ranges.

The SMIORS 100 can further include the refractometer 130 to generate a refractive mapping of the imaged region. The refractometer 130 may be any of the widely used types, including a laser ray tracer, a Shack-Hartmann, a Talbot-Moire, or another refractometer. The refractometer 130 can include a wavefront analyzer, an aberration detector, or an aberrometer. Some references use these terms essentially interchangeably or synonymously. A dynamic range of the refractometer 130 can cover both phakic and aphakic eyes, i.e. the eyes with and without the natural lens. Embodiments of the refractometer 130 will be discussed at greater length in relation to FIGS. 2A-D.

In some SMIORS 100 the OCT imaging system 120 and the refractometer 130 can be integrated via a microscope interface 150 that can include a (down-) beamsplitter 152d to provide an optical coupling into the main optical pathway of the microscope 112 or slit-lamp. A mirror 154-1 can couple the light of the refractometer 130 into the optical path, and a mirror 154-2 can couple the light of the OCT 120 into the optical path. The microscope interface 150, its beamsplitter 152d, and mirrors 154-1/2 can integrate the OCT imaging system 120 and the refractometer 130 with the eye-visualization system 110.

In embodiments, where the OCT imaging system 120 operates in the near infrared (IR) range of 900-1,400 nm, and the refractometer operates in the 700-900 nm range, the beamsplitter 152d can be close to 100% transparent in the visible range of 400 nm-700 nm, and close to 100% reflective in the near-IR range of 700-1,400 nm range for high efficiency and low noise operations.

By the same token, in a SMIORS 100 where the mirror 154-1 redirects light into the refractometer 130, the mirror 154-1 can be close-to-100% reflective in the near IR range of 700-900 nm, and the mirror 154-2 can be close-to-100% refractive in the near IR range of 900-1,400 nm, redirecting to the OCT imaging system 120. Here, "close-to-100%" can refer to a value in the 50-100% range in some embodiments, or to a value in the 80-100% range in others.

In some specific embodiments, the beamsplitter 152d can have a reflectance in the 50-100% range for a wavelength in the 700-1,400 nm range, and a reflectance in the 0-50% range for a wavelength in the 400-700 nm range.

FIG. 1 shows that the SMIORS 100 can include a second, up-beam splitter 152u besides the down-beam splitter 152d. The down-beam-splitter 152d can direct light between the objective 113 and the integrated OCT 120/refractometer 130 ensemble. The up-beam-splitter 152u can direct light between a display 160 and the binocular 117, as described below.

The analyzer, or controller, 140 can perform the integrated biometrical analysis based on the received OCT and refractive information. The analysis can make use of a wide variety of well-known optical software systems and products, including ray tracing software and computer-aided design (CAD) software. The result of the integrated biometry can be (1) a value of the optical power of portions of the eye and a corresponding suggested or prescribed diopter for a suitable IOL; (2) a value and an orientation of an astigmatism of the cornea, and suggested or prescribed toric parameters of a toric IOL to compensate this astigmatism; and (3) a suggested or prescribed location and length of one or more relaxing incisions to correct this astigmatism, among others.

The analyzer 140 can output the result of this integrated biometry towards the display 160, so that the display 160 can display these results for the surgeon. Display 160 can be an electronic video-display or a computerized display, associated with the eye-visualization system 110. In other embodiments, the display 160 can be a display in close proximity of the microscope 112, such as attached to the outside of the microscope 112. Finally, in some embodiments, display 160 can be a micro-display, or heads-up display, that projects the display light into the optical pathway of the microscope 112. The projection can be coupled into the main optical pathway via a mirror 157. In other embodiments, the entire heads-up display 160 can be located inside the microscope 112, or integrated with a port of the microscope 112.

FIG. 1 illustrates such an embodiment, where the display 160 is a heads-up display that projects the biometric information back towards the microscope interface 150 via the mirror 157. In such embodiments, microscope interface 150 may contain two beam splitters, down-beam splitter 152d and up-beam splitter 152u. The down-beam splitter 152d can redirect the light of the OCT 120 and the refractometer 130 towards the patient's eye and redirect the light from the eye 10 towards the OCT 120 and refractometer 130. The up-beam-splitter 152u can redirect the display light from the heads-up display 160 towards the binocular or ocular 117 of the microscope, so that the surgeon can view the displayed biometric information intra-operatively and make informed decisions based on this displayed biometrics.

Figure 2A:
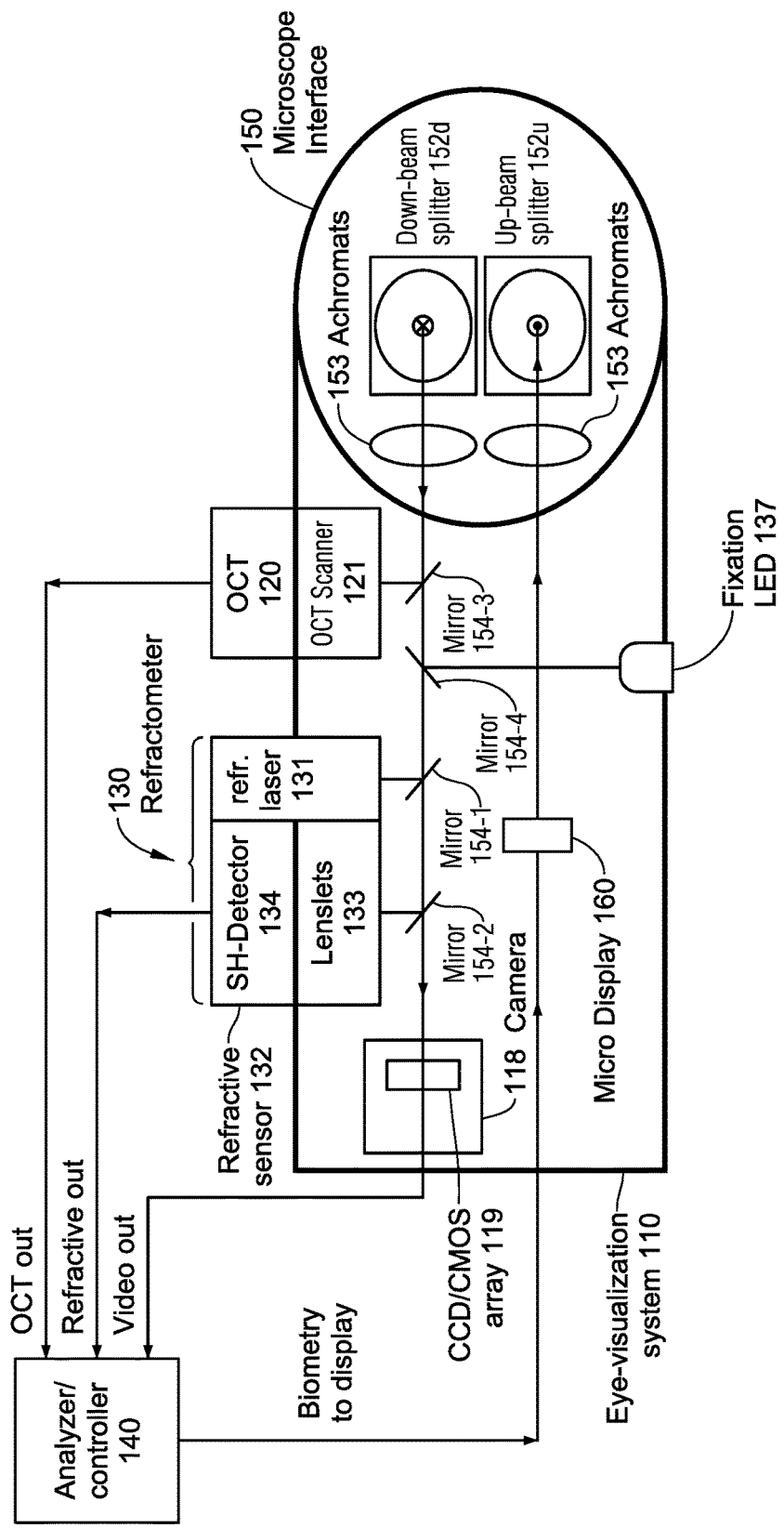
FIGS. 2A-D are diagrams illustrating embodiments of Slit lamp-or-Microscope-Integrated-OCT-Refractometer System.

FIG. 2A illustrates an embodiment of the refractometer 130 that involves a Shack-Hartmann (SH) refractometer 130. The SH refractometer 130 can include a refractive laser source 131, whose light is coupled into the main optical pathway of the surgical microscope 112 through the mirror 154-1, and the microscope interface 150. As described above, in embodiments where there are two beam splitters, the light of the refractometer 130 can be directed to a down-beam-splitter 152d that redirects the light towards the objective 113 and the patient's eye 10. In these two-beam-splitter embodiments, the microscope interface 150 can include two achromatizators 153, or achromats 153 for short.

The light that is returned from the imaged region of the eye 10 can be redirected by the same down-beam-splitter 152d and reach mirror 154-2, where it can be reflected to a refractive sensor 132 that can include a lenslet array 133 to receive the refractive light beam returned from the imaged region and to decompose it into beamlets. The lenslet array 133 can focus the beamlets onto a SH-detector 134, or detector-array 134 that can detect the beamlets individually and to perform the refractive mapping of the imaged region based on the detected beamlets. The SH-detector or SH-detector array 134 can output a "refractive out" signal, carrying the refractive information computed from the detected beamlets. The refractive mapping of the imaged region itself, based on the detected beamlets, can be performed by a processor directly associated with the refractometer 130. In other embodiments, the detected beamlet signals can be forwarded to the separate analyzer/controller 140 to perform the refractive mapping.

The light of the OCT imaging system 120 can be scanned via an OCT scanner 121, and then coupled into the main optical pathway at a mirror 154-3, redirected to the down-beam-splitter 152d of the microscope interface 150. The returned OCT light can be redirected from the main optical pathway by the mirror 154-3 and then fed into a fiber optics as the "OCT out" signal, guided to an external OCT interferometer and electronics that is located in an external console. In some embodiments, the OCT interferometer and OCT electronics can be part of the analyzer/controller 140. In other embodiments, the OCT interferometer and OCT electronics can be a separate block.

The eye-visualization system 110 can further include the camera 118 that can include a CCD or CMOS array 119 to generate a digital image that can be outputted as "video out". CMOS cameras typically work faster than CCD cameras. This can be advantageous to deliver closer-to-real-time imaging and intra-operative information for the surgeon.

In some SMIORS 100 embodiments, several rays can share the same optical pathway. For example, the light of the refractometer 130, that of the OCT 120 and the light used by the camera 118 can all share the same pathway in some embodiments. Therefore, in some embodiments the returned light is decomposed so that the light-components are redirected to the corresponding sensors and detectors. For example, in FIG. 2A, mirror 154-3 redirects the OCT light to the OCT system 120, mirror 154-2 redirects the refractive light to the refractometer 130, and the remaining light can reach the camera 118.

This functionality can be achieved by a suitable spectral design. For example, the OCT 120 can be designed to operate with an OCT laser light in the 900-1,400 nm wavelength range. The refractometer 130 can operate with a refractive laser light in the 700-900 nm range. Finally, the camera 118 can operate with the visible spectrum of 400-700 nm range. Thus, a spectral design can separate and decompose the light returned from the imaged region if the mirror 154-3 is reflective in the 900-1,400 nm range but transmissive at shorter wavelengths, and the mirror 154-2 is reflective in the 700-900 nm range but transmissive at shorter wavelengths. Such a spectral design can make sure that the appropriate components of the returned light reach the OCT 120, refractometer 130 and camera 118.

It is noted that the light of the refractive laser 131 is also coupled into the beam path by the mirror 154-1. For the system 100 to function properly, this mirror 154-1 can be half-reflective in the 700-900 nm range, so that it lets half of the returned refractive light through to reach the mirror 154-2 that redirects this light into the refractive sensor 132.

Besides the mirrors 154-1/4, the beam splitters 152u/d can also have a suitable spectral design. In some embodiments, the refractometer 130 can operate with a wavelength in the 700-900 nm range, and be coupled in the an optical pathway of the eye-visualization system 110 via the beam splitter 152d that has a reflectance in the 50-100% range for a wavelength in the 700-900 nm range.

In some of these embodiments, the OCT imaging system 120 can operate with a wavelength in the 900-1,400 nm range, and be coupled in the an optical pathway of the eye-visualization system 110 via the beam splitter 152d that has a reflectance in the 50-100% range for a wavelength in the 900-1,400 nm range.

Embodiments of SMIORS 100 can be constructed with many other spectral designs. The wavelength ranges, the transmissive properties, the reflective properties, and the sequence of optical elements can take a wide variety of arrangements, while maintaining the described functionalities.

In particular, the sequence of the camera 118, OCT 120 and refractometer 130 along the optical pathway can be any sequence depending on the considerations of the spectral design. In some of these embodiments, mirrors with transmissive wavelength-widows may need to be employed, transmitting light within a wavelength range and reflecting above and below that range. E.g., in some embodiments, the refractometer 130 can be the first and the OCT 120 can be positioned after the refractometer 130 in the optical pathway.

As discussed above, the analyzer 140 can receive the "OCT out" and "Refractive out" signals. In some embodiments, the analyzer 140 can even use the "Video out" signal from the camera 118. The analyzer, or controller, 140 can use a wide variety of optical analytic software to analyze these input signals with an existing eye-model, with a modified eye-model, or with a custom eye model.

The eye model can be an Emsley model, a Greivenkamp model, a Gullstrand model, a Helmholtz-Laurence model or a Liouu-Brennan model, among others. The determined parameters of the eye model can include a spherical parameter, a cylinder parameter, including one or more radii of curvatures, and an orientation angle of the lens and the cornea. The analyzer 140 can be programmed to determine these parameters by executing a ray-tracing software. With these software products and the "OCT out" and "Refractive out" signals, the analyzer can perform an integrated biometric analysis.

The analyzer 140 can perform this analysis with a processor and a memory that can be programmed to determine parameters of an eye model using both the OCT image and the refractive mapping. Part of the analysis can be that the analyzer registers the OCT image and the refractive mapping. For example, the OCT image can provide a cross sectional image of the cornea that can be used to determine a corneal curvature. An angular dependence of the corneal curvature can be extracted by performing OCT B-scans in several directions. In parallel, the refractive mapping can provide information about the optical properties of the cornea. Combining the refractive and OCT images therefore can develop a detailed characterization of an astigmatism of the cornea.

The outcome of this analysis can be a refractive characteristic of the eye itself. In some embodiments, the analyzer 140 can be configured to determine the refractive characteristics of the procedure eye 10 by determining some or all parameters of one of the above eye models for the procedure eye. This can be viewed as the analyzer 140 individualizing an eye model for the eye of the particular patient.

Once the parameters of the eye model have been determined by the analyzer 140, the analyzer 140 can proceed to perform the biometric analysis. This biometric analysis can be performed at several different stages, including: (1) during an office visit substantially before the surgery, (2) during surgical preparations in the surgical theater, just before surgery commences, (3) after surgery has started and relaxing incisions have been created, but before the IOL insertion has started, (4) after the surgery has started and the cataractous nucleus has been removed but before the IOL insertion has started, and (5) after the IOL insertion has started.

In stages (1) and (20, in some embodiments, the analyzer can select from a database of available Intra Ocular Lenses (IOLs) to achieve a desired optical correction of the procedure eye 10 when inserted into the procedure eye 10. The desired optical correction can be related to at least one of the following characteristics of the procedure eye 10: a refractive error, an astigmatism, an optical power, a higher order aberration, a coma, a Zernike coefficient, a centration, and a tilt.

In some embodiments, the analyzer 140 can be configured to determine a recommended/prescribed IOL optical power, or a value and orientation of astigmatism of a toric IOL, a multifocal characteristic, and a position of an Intra Ocular Lens (IOL) in a capsule of the eye to achieve the desired optical correction of the eye.

Some fast SMIORS 100 embodiments may be configured to perform intra-operative biometry in stages (3)-(5). In some embodiments, the analyzer 140, together with the OCT imaging system 120 and the refractometer 130, can include a programmed processor and memory to determine the refractive characteristics of the eye within 10 seconds. Such fast SMIORSs 100 can provide biometric and refractive information intra-operatively, a feature that can be very useful to assist the surgeon to optimize the refractive surgical outcome.

In some embodiments, the analyzer 140, including a processor and a memory, can be programmed to determine eye-model-parameters from the OCT image and the refractive mapping in stage (3), i.e. after a relaxing incision has been created in an ophthalmic tissue, and to output correcting biometry information to the display 160 when the determined eye-model-parameters are different from pre-operatively determined eye-model-parameters.

In some embodiments, the analyzer 140, including a processor and a memory of the analyzer 140, can be programmed to determine eye-model-parameters from the OCT image and the refractive mapping of the aphakic eye in stage (4), i.e. after a natural lens has been removed from the eye. The analyzer 140 can output correcting biometry information to the display 160 when the determined eye-model-parameters are different from pre-operatively determined eye-model-parameters.

In some embodiments, the analyzer 140 can be programmed to determine eye-model-parameters from the OCT image and the refractive mapping in stage (5), i.e. after an insertion of an IOL lens into a capsule of the eye has started; and to output biometry information to a display to adjust at least one of a centration and a toric orientation of the IOL being inserted.

The OCT imaging, refractive mapping and biometric analysis can be performed by various functional blocks. Some of the imaging functions can be performed by a processor that is associated with the OCT imaging system 120, other imaging functions by the analyzer 140. Some of the refractive mapping functions can be performed by a processor that is associated with the refractometer 130, other refractive mapping functions by the analyzer 140.

Once the biometric analysis is performed, analyzer 140 can send the corresponding information and signals to the display 160. In the embodiment of FIG. 2A, the display 160 is a micro-display, or heads-up display 160 that projects the biometric information back into the optical pathway of the SMIORS 100. In such a SMIORS 100, the display beam can be directed to the up-beam-splitter 152u that can redirect the display beam to the surgeon through the binocular/ocular 117. Such a design enables the surgeon to maintain the visual observation of the surgical process while also viewing the biometric information of the heads-up display.

Finally, a fixation LED 137 can be included in some embodiments, to provide a visible fixation light for the patient to fixate on. The patient doing so helps the surgeon to maintain alignment of the SMIORS 100 and the patient's eye 10. The light of the fixation LED 137 can be coupled into the optical pathway through a mirror 154-4. In light of the above considerations, the wavelength of the fixation LED 137 and the wavelength-dependence of the reflective properties of the mirror 154-4 can be chosen based on the considerations of the spectral design of the other components. For example, the wavelength can be a narrowly defined peak in the visible spectrum of 400-700 nm.

Figure 2B:
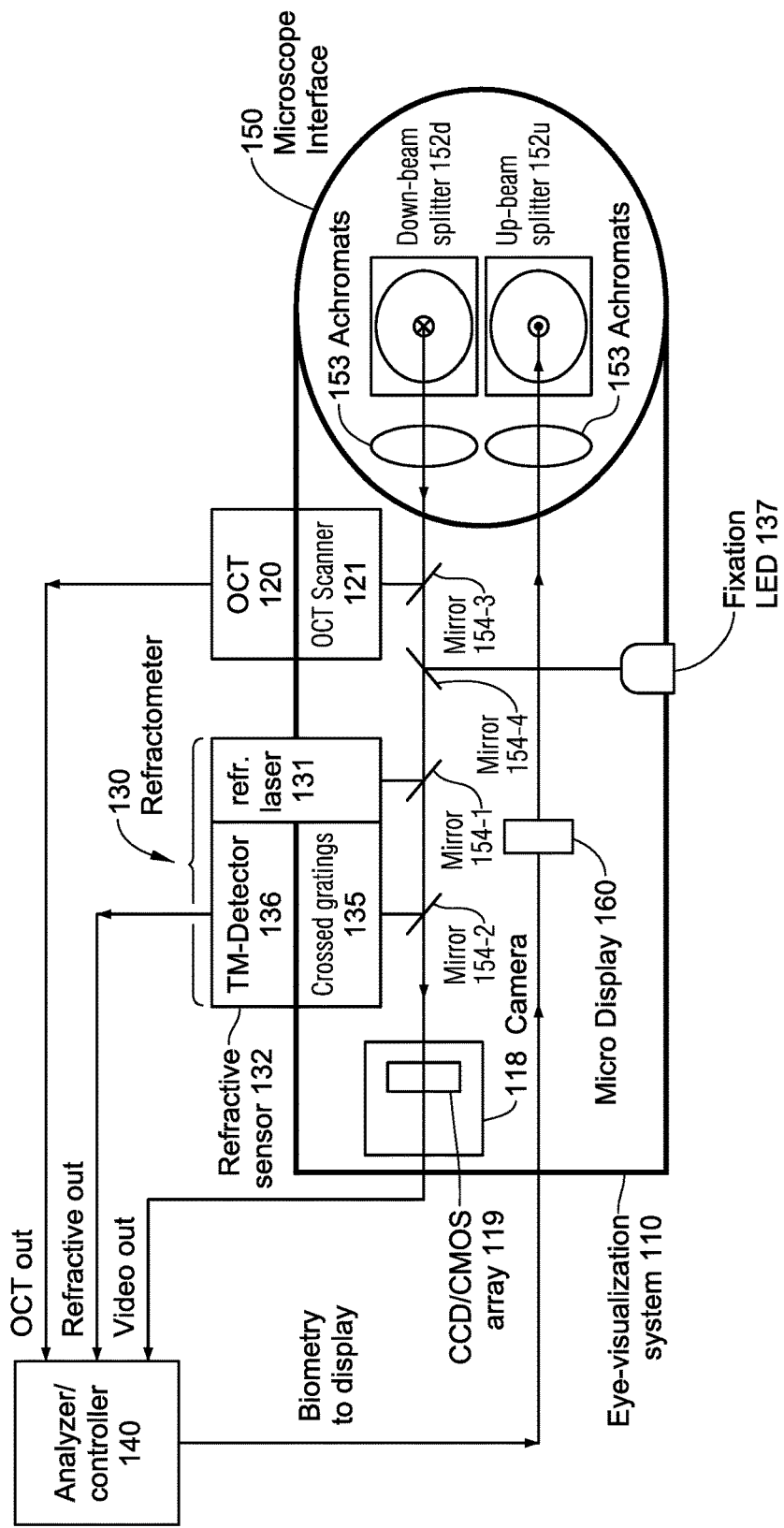

FIG. 2B illustrates that other embodiments of the refractometer 130 can involve a Talbot-Moire (TM) refractometer. The TM refractometer 130 can again include a refractive laser source 131, configured to generate a laser beam to be directed to the imaged region partially through an optical pathway of the surgical microscope 112. The refractive laser beam can be coupled into the optical pathway through the mirror 154-1. The beam can be subsequently coupled into the main optical pathway of the surgical microscope of the eye-visualization system 110 through the microscope interface 150. In some embodiments, the microscope interface 150 can include one or two beam splitters 152 and a corresponding number of achromatizators 153. In two beam-splitter embodiments, the light of the refractometer 130 can be coupled into the main optical pathway through the down-beam-splitter 152d.

In addition, the TM embodiment 130 can also include the refractive sensor 132 that in this embodiment includes two crossed gratings 135 with a variable relative angle to receive the beam returned from the imaged region, and to output a Moire pattern corresponding to the received beam. The refractive sensor 132 can also include a detector 136 to detect the Moire pattern, and to perform the refractive mapping of the imaged region based on the detected Moire pattern. The rest of the embodiment can be analogous to the embodiment of FIG. 2A.

Figure 2C:
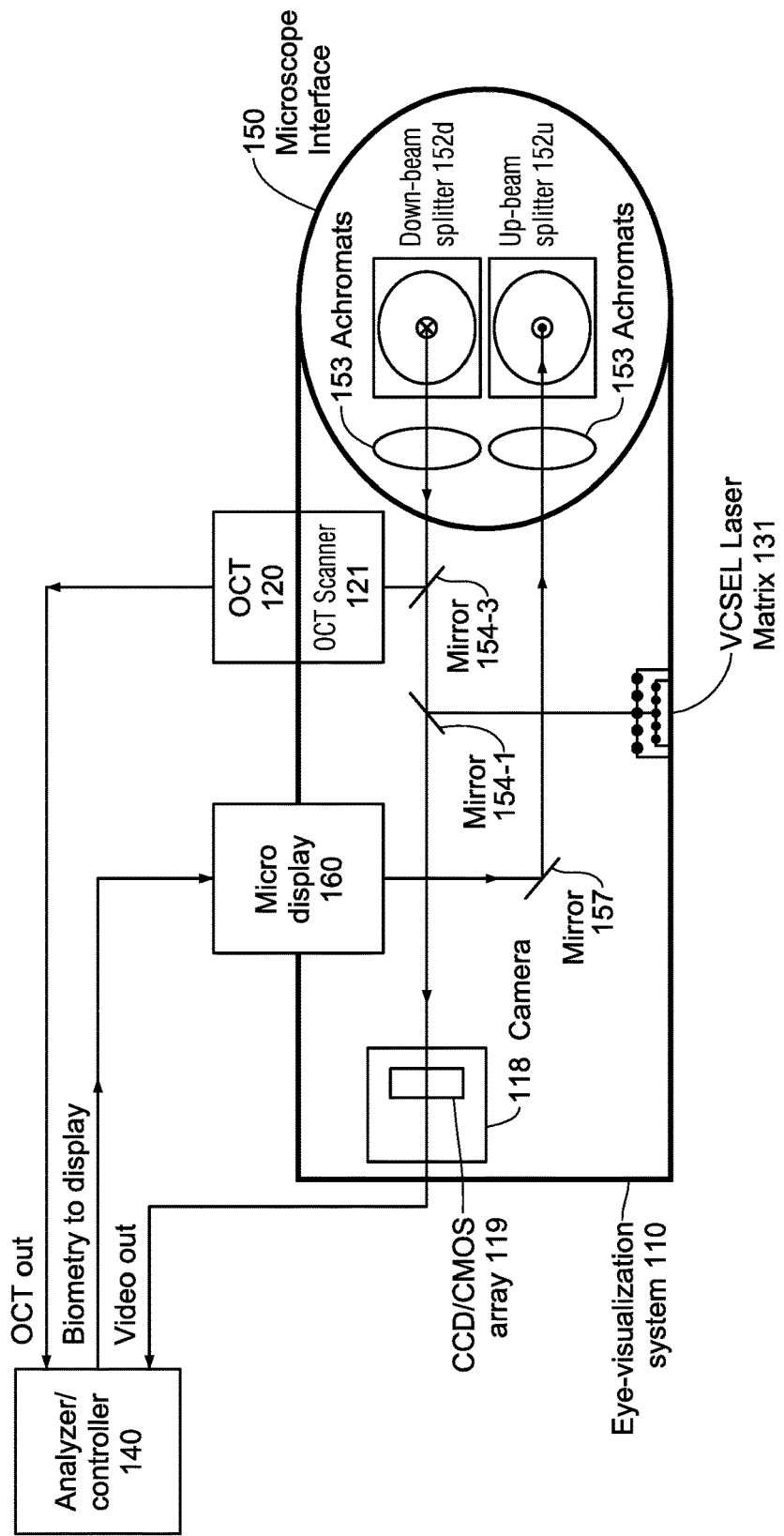

FIG. 2C illustrates another embodiment of the SMIORS 100. This embodiment shares several elements with the embodiments of FIGS. 2A-B that are analogously numbered. In addition, an embodiment of the refractometer 130 can be a laser ray tracing system. (It is noted here that the term "laser ray tracing" refers to a hardware implementation of the refractometer 130, which involves scanning the rays of the refractive laser beam with hardware means, such as with scanners. The term "ray tracing" is also used, however, in describing the software of the optical modeling, performed by the analyzer 140. As a matter of clarification, the software-implemented ray tracing method can be used with any and all embodiments of the refractometer 130, including those in FIGS. 2A-D, not only with the laser ray tracing embodiment of FIG. 2C.)

The laser source 131 of the refractometer 130 can include a set of vertical cavity surface emitting lasers (VCSELs), or another similar matrix laser source. The VCSEL matrix 131 can, for example, have 16×16 individual VCSEL lasers that can emit short pulses in sequence. This sequence of pulses creates the equivalent of a single laser light, scanned along a scanning pattern. One of the advantages of VCSEL lasers is that by varying the firing sequence of individual VCSEL lasers, a wide variety of scanning patterns can be generated with minimal adjustments.

The "scanned beam" of the VCSEL matrix 131 can be coupled into the optical pathway of the microscope 112 via the mirror 154-1, on its way to the down-beam-splitter 152d, getting redirected to the patient's eye.

As the refractive light returns from the imaged region, in the ray-tracer embodiment 130 the camera 118 can play the role of the refractive sensor 132 in the following manner. The VCSEL laser matrix 131 can be used to generate a circular "scan pattern" by firing the individual VCSEL lasers is a circular pattern. The ray-tracing refractometer 130 can scan a refractive laser along a loop to direct the scanned refractive laser to the imaged region, and to record a path the refractive laser sweeps in the imaged region during the scanning. If the patient's eye is emmetropic, i.e. free of refractive errors, then throughout the scan, the "beam" will remain focused to one spot on the macula. In other words, in an emmetropic eye the pulses of each individual VCSEL laser of the VCSEL laser matrix 131 hit the same spot, indicating the absence of a refractive error.

Eyes can have at least two types of refractive errors: the scanned beam can be over-focused or under-focused, i.e. focused proximal to the retina or distal to the retina, respectively. Over-focused beams are said to have a positive refractive error, under-focused beams a negative error. In both of these cases, as the VCSEL laser is "scanned" along a ring or loop, the beam focused by the eye will scan along a ring of laser spots on the fundus. The larger the ring diameter, the larger the refractive error.

The sign of the refractive error determines the phase between the "scanning" of the VCSEL laser and the scanning of the focused laser spots appearing on fundus. The under-focused beams in an eye with negative refractive errors do not cross. In such eyes, the VCSEL lasers and the spots scanned on the fundus are in phase. For example, if the VCSEL lasers fire in a clock-wise ring sequence, then the laser spots on the fundus will be scanned in a clock-wise ring sequence as well.

In contrast, the over-focused beams of an eye with positive refractive errors cross before they reach the retina. In such eyes, if the VCSEL lasers fire in a clock-wise ring sequence, the laser spots on the fundus will be scanned in a counter-clockwise ring sequence.

In both cases, the camera 118 can play the role of the refractive sensor 132. In the outputted "Video out" signal, the camera can indicate the radius or size of the ring or path scanned by the laser spots on the fundus. This can allow the determination of the degree or magnitude of the refractive error. The camera can also indicate whether the scanning or firing sequence of the VCSEL lasers and the scanning of the spot on the fundus are in phase or in opposite phase.

Using the "Video out" signal from the camera 118, the analyzer 140 can be configured to determine an optical power of the eye, or a portion of the eye, from a size of the recorded path, and to determine a sign of the optical power of the eye from a phase of the recorded path.

In some embodiments, the determination of the two scans moving in-phase or out-of-phase can be performed by a position-sensor, sometimes without using the CMOS array 119. The position-sensor of the camera 118 can track the detection signal in a low number of pixels, such as four, and can output a low-resolution representation whether the fundus scan or path is in- or out-of phase with the loop scan of the refractive VCSEL laser. Such position sensors provide only low-resolution information, but they do so much quicker than full cameras.

Finally, for eyes which have a refractive error with a cylindrical component, the circular/loop scan of the VCSEL laser can cause the spot on the fundus scan along an ellipse path. The angle of ellipse's long axis determines the astigmatism angle. The relative sizes of the short and long axii, and their aspect ratio, indicate the spherical and cylindrical errors.

In all these described cases, the camera 118, possibly in combination with a quadrant-based position sensor, can serve as the refractive sensor 132. Accordingly, the camera 118 in such ray-tracer embodiments can be viewed as part of the refractometer 130. The "video out", or "refractive/video out" data from the camera 118 can be forwarded to the analyzer 140. The analyzer 140 can also receive the "OCT out" signal from the OCT 120. Integrating these data, the analyzer 140 can determine some biometric or refractive information to display. This "biometry to display" signal then can be outputted by the analyzer 140 toward the display 160. In the embodiment of FIG. 2C, the display 160 can be a micro-display, or heads-up display 160 that projects the biometric information into the optical pathway of the microscope 112 via the up-beam-splitter 152*u*, so that it reaches the surgeon through the binocular or ocular 117.

Figure 2D:
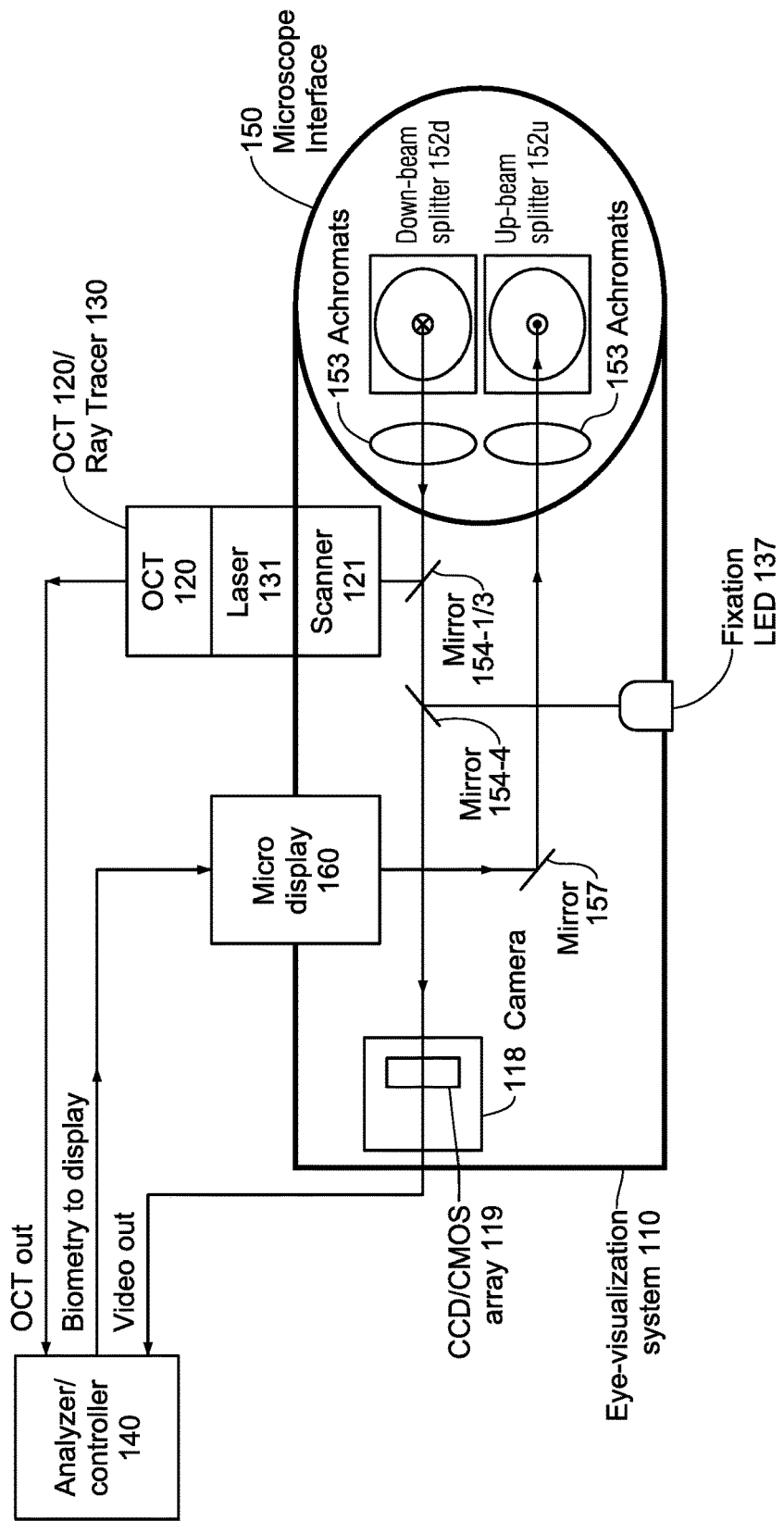

FIG. 2D illustrates yet another embodiment of SMIORS 100. This embodiment shares several elements with the embodiments of FIGS. 2A-C that are analogously numbered. This embodiment of the refractometer 130 is also a laser ray-tracing system, but one that is integrated with the OCT imaging system 120 even closer. The light, generated by the refractive laser 131, can be coupled into the scanner 121 that is shared with the OCT imaging system 120. In other embodiments, the ray tracer 130 can have its own scanner. The scanner 121 can sequentially direct the laser ray along a scanning pattern into the imaged region. Thus, the shared scanner 121 of the OCT system can replace, or switch-out, the VCSEL laser matrix scanning system 131 of FIG. 2C. One of the features of this switch-out is that in VCSEL systems it can be a challenge to focus the lights of each individual laser of the laser matrix properly, since they are generated at different points of the matrix. In contrast, embodiments of FIG. 2D have a single laser source 131, helping the focusing.

As before, the scanned refractive laser light can be coupled by the mirror 154-1/3 into the shared optical pathway, and by the down-beam-splitter 152*d* into the main optical pathway of the microscope 112. As for the embodiment of FIG. 2C, the returned scanned refractive light can be received and detected by the camera 118.

The refractive analysis can be performed based on the scanner 121 scanning the refractive laser beam in a circle, ring or loop, and the camera 118 recording the diameter and phase of the path scanned, or swept, by the spot of the refractive laser beam on the fundus. The output of the camera 118 can be coupled into the analyzer 140 as the "refractive/video out" signal, just as the OCT image or data from the OCT system 120 as the "OCT out" signal. Then the analyzer 140 can perform the integrated biometry analysis based on these signals. The result of the integrated analysis can be forwarded to the display 160 as the "biometry to display" signal. The heads-up display, or micro-display 160 can project the received biometry information into the main optical pathway of the microscope 112 via the up-beam-splitter 152*u* of the microscope interface 150.

In the above embodiments of FIGS. 2A-D, the OCT imaging system 120 and the refractometer 130 can be coupled into the surgical microscope 112 of the eye-visualization system 110 proximal to the distalmost lens of the microscope, thereby avoiding a reduction of a microscope-eye working distance. In some embodiments this can be achieved by coupling the OCT imaging system 120 and the refractometer 130 into the surgical microscope 112 through at least one beam-splitter port of the surgical microscope. Such embodiments are capable of limiting the increase of the height of the microscope oculars or binoculars 117 by less than 2 inches, or even by less than 1 inch.

Returning to the existing needs for intra-operative use, articulated in points 6-8 earlier, embodiments of the SMIORS 100 can be used to perform an integrated analysis of the OCT and refractive information at stage (3). This can be a test of the freshly-formed relaxing incisions that were prescribed based on a pre-operative analysis. It can happen in some cases that the relaxing incisions that were prescribed based on the pre-operative analysis resulted in a refractive correction that was slightly different from the planned one. Performing the intra-operative biometry in stage (3), can give the surgeon a chance to execute a corrective action, such as to change the previously determined optical power of the IOL to be inserted to a different one to additionally compensate the small un-planned deviation caused by the relaxing incision.

Embodiments of the SMIORS 100 can also be used to perform an integrated analysis of the OCT and refractive information of an aphakic eye, from which the cataractous lens has been removed. Performing biometry at this stage (4) can be very useful to test the pre-operatively developed modeling of the eye now that the cataractous lens has been removed and the optical signals are not blurred by the cataract. This biometric analysis after the removal of the cataractous lens but before the IOL insertion provides a final stage where the surgeon can change the optical power of the IOL to be inserted in light of the new biometry.

Finally, in some cases the intra-operative biometry can be performed not only after the removal of the cataractous lens, but at stage (5): after the insertion of the IOL has been started by the surgeon. In such embodiments, for example, the surgeon may have started to insert a toric IOL into the lens capsule. An intra-operative biometry can be performed during the process to check whether the orientation of the major axis of the toric IOL is indeed oriented in the direction prescribed by the pre-operative diagnosis and prescription. Further, this procedure can also check whether the modeled direction of the toric IOL indeed works as optimally as the pre-surgical modeling has suggested. In a real-time intra-operative biometry analysis, the analyzer 140 can discover that a change of the direction of the axis of astigmatism of the already inserted toric IOL may improve the overall optical performance of the eye.

After the analyzer 140 has performed any of these stage (3)-(5) intra-operative biometric analyses, the analyzer 140 may direct the heads-up display 160 to display a suggested rotation of the orientation of the toric IOL for the surgeon in the shared optical pathway of the surgical microscope 112. In response, the surgeon can immediately adjust the IOL insertion process accordingly, without ever removing her or his eye from the microscope 112.

In some analogous embodiments, the SMIORS 100 can include an intra-operative biometer 100, comprising: a surgical microscope 112, configured to provide a visual image of a imaged region in an eye; an Optical Coherence Tomographic (OCT) imaging system 120, configured to generate an OCT image of the imaged region; a refractometer 130, configured to determine refractive information of the imaged region; an analyzer 140, configured to determine biometric information of the eye based on the OCT image and the refractive information; and a heads-up display 160, configured to display the determined biometric information in an optical pathway of the surgical microscope 112. In some embodiments the determined biometric information can be displayed intra-operatively.

Figure 3A:
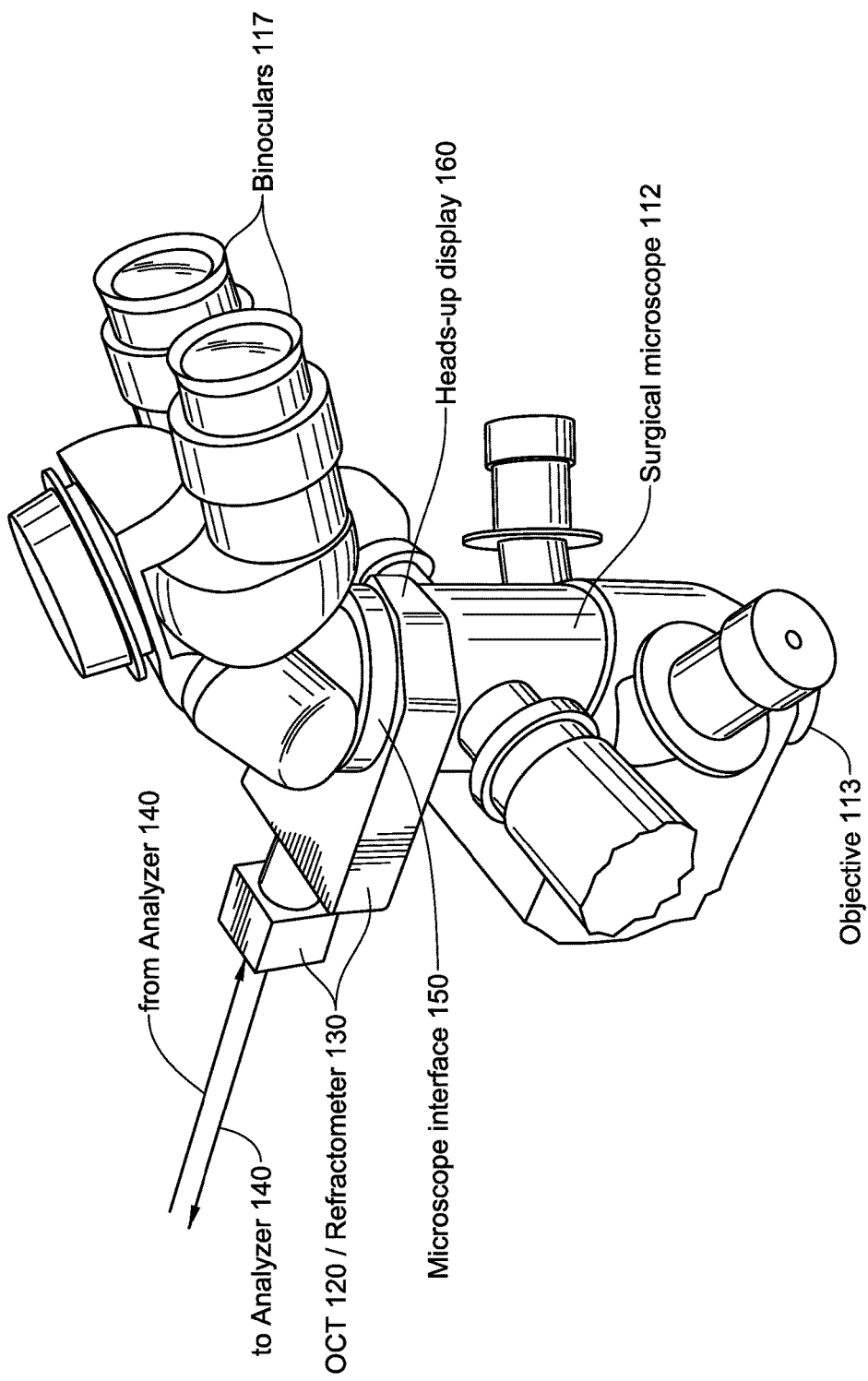
FIG. 3A-C are diagrams illustrating a particular embodiment of a microscope with an Integrated-OCT-Refractometer System.
Figure 3B:
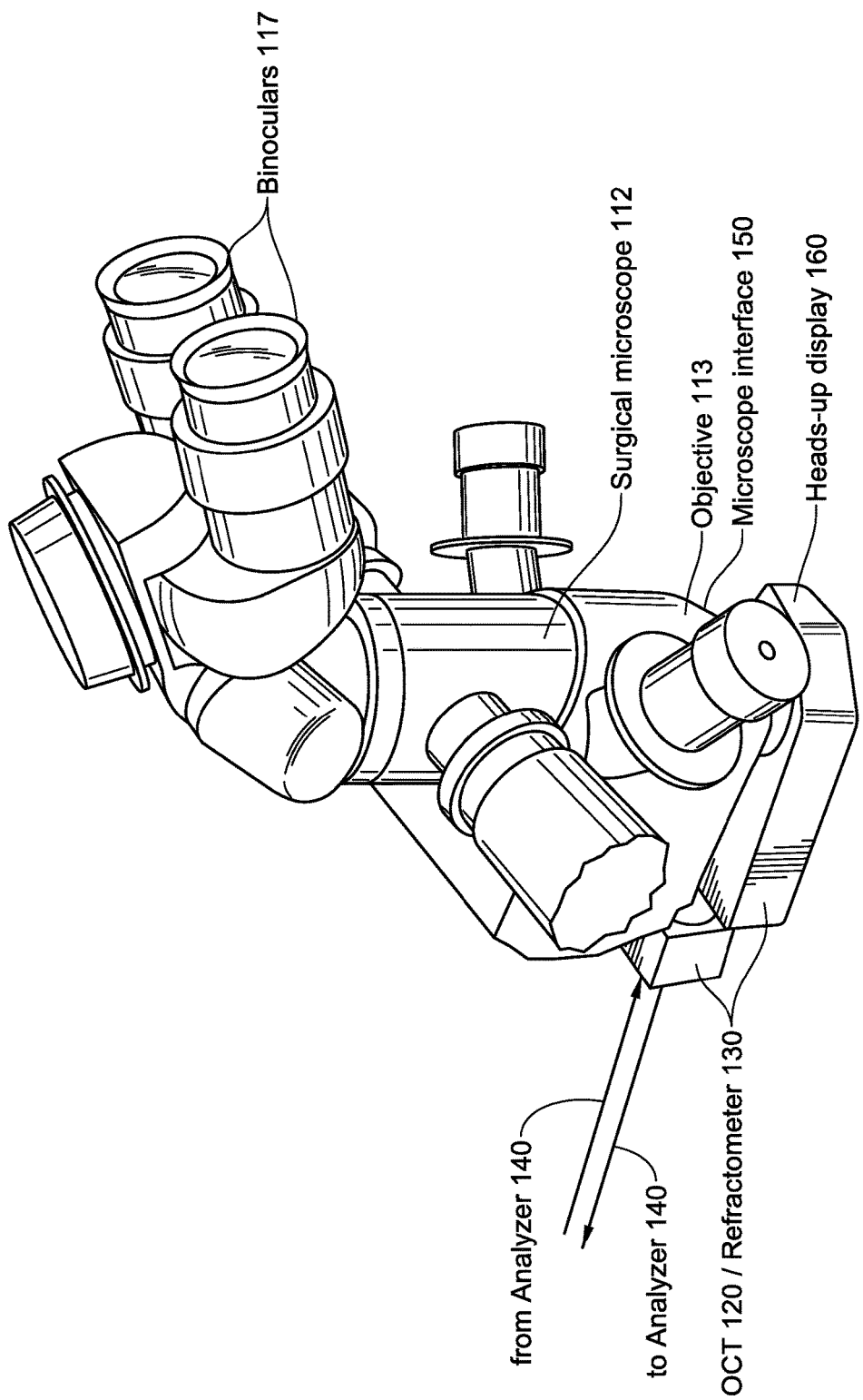
Figure 3C:
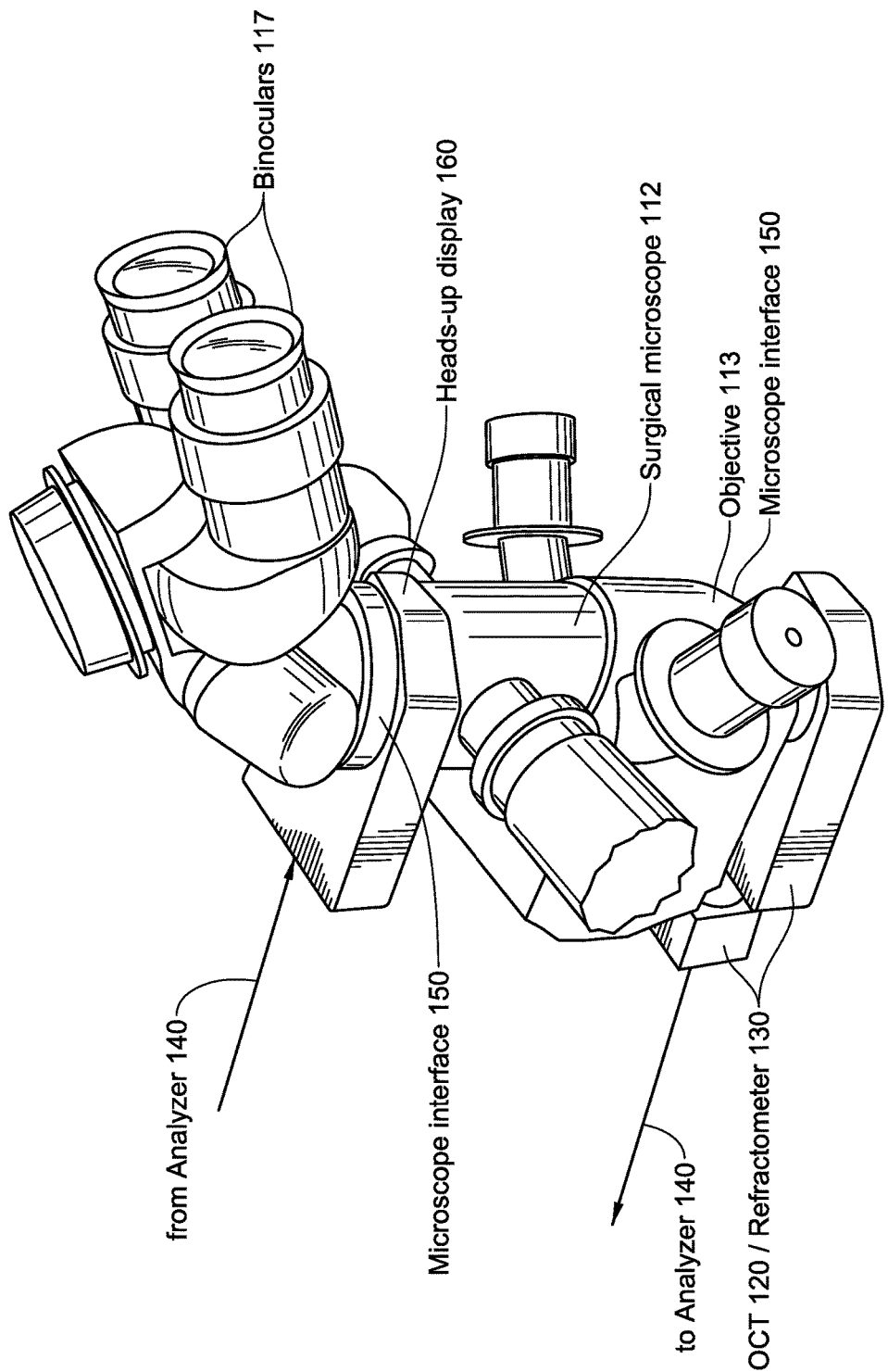

FIGS. 3A-C illustrate embodiments of the SMIORS 100 or intra-operative biometer 100. The eye-visualization system 110 in this embodiment can include a surgical microscope 112 that has an objective 113 and a binocular 117. The OCT imaging system 120 and the refractometer 130 can be integrated into the SMIORS 100 via the microscope interface 150. The OCT imaging information and the refractive mapping can be forwarded to the analyzer 140 that can be disposed external to the eye-visualization system 110. The analyzer 140 can perform an integrated biometric analysis based on the OCT image and the refractive mapping, and generate a biometric information. The analyzer 140 can signal the determined biometric information to the heads-up display 160 that is configured to display the determined biometric information in an optical pathway of the surgical microscope 112.

FIG. 3A illustrates an embodiment where the microscope interface 150 is located relatively far from the distal objective of the microscope 112. FIG. 3B illustrates an analogous embodiment, differing in that the microscope interface 150 is located at a more distal position. Finally, FIG. 3C illustrates a mixed embodiment. Here, the OCT 120 and the refractometer 130 can be integrated into a distal microscope interface 150, whereas the heads-up display can be coupled to the microscope 112 at a proximal location.

Figure 4:
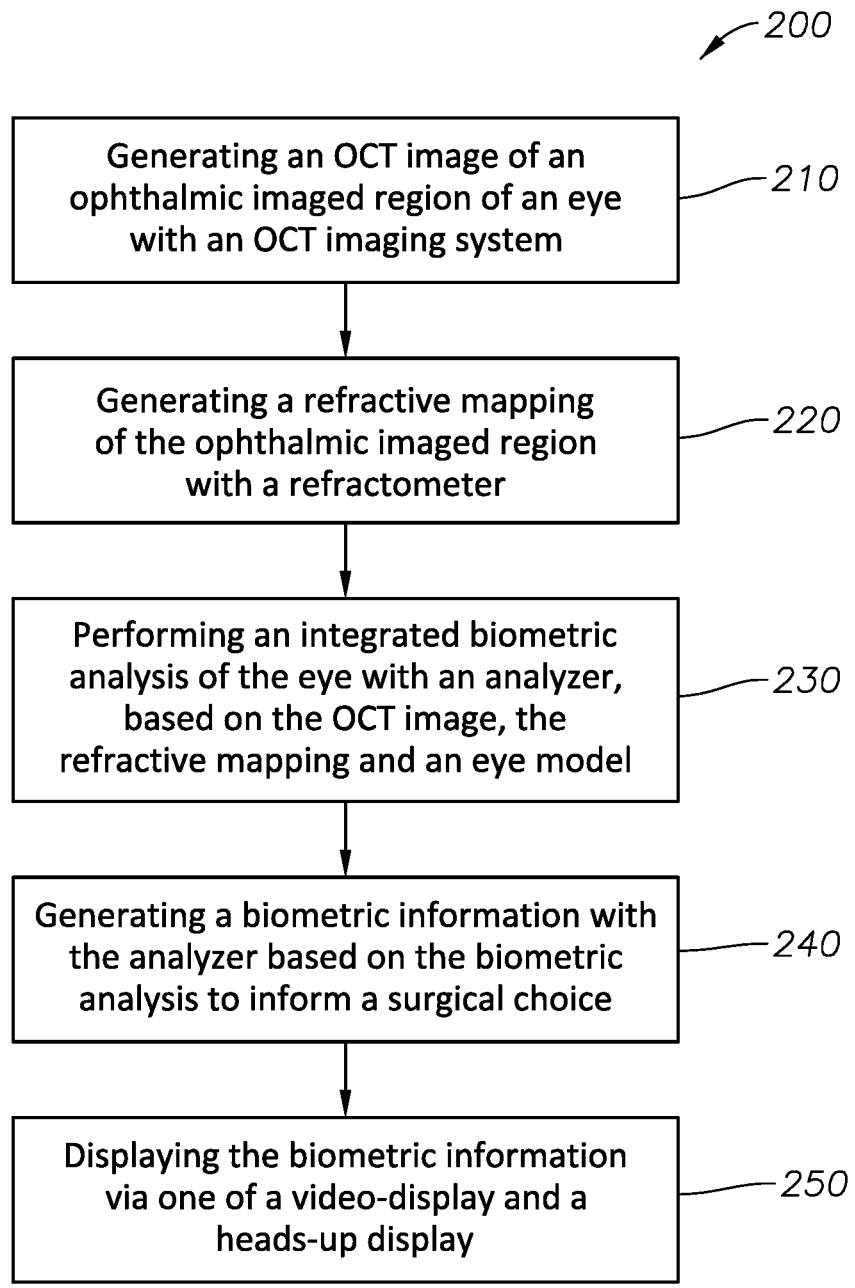
FIG. 4 illustrates a method of operating an integrated OCT-Refractometer system.

Finally, FIG. 4 illustrates a method 200 of operating embodiments of a SMIORS 100. The method 200 can include:

210: generating an OCT image of an ophthalmic imaged region of an eye with an OCT imaging system, e.g. the OCT imaging system 120;

220: generating a refractive mapping of the ophthalmic imaged region with a refractometer, e.g. the refractometer 130;

230: performing an integrated biometric analysis of the eye with an analyzer, e.g. the analyzer 140, based on the OCT image, the refractive mapping and an eye model;

240: generating a biometric information with the analyzer based on the biometric analysis to inform a surgical choice; and 250: displaying the biometric information via one of a video-display and a heads-up display, e.g. the display 160.

Embodiments as described herein provide a slit lamp or microscope integrated OCT and Refractometer. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. A method for determining refractive characteristics of an eye, comprising:
   receiving, from an Optical Coherence Tomographic (OCT) imaging system, OCT image data of an imaged region of the eye;
   receiving, from a refractometer, refractive mapping data of the imaged region;
   registering, by a processor configured to execute optical analytic software, the OCT image data and the refractive mapping data;
   combining, by the processor, the OCT image data and refractive mapping data; and
   executing, by the processor, optical ray tracing software to determine the refractive characteristics of the eye based on the combined OCT image data and refractive mapping data; and
   displaying biometric information indicating the determined refractive characteristics of the eye.

2. The method of claim 1, wherein the refractometer comprises at least one of a Shack-Hartmann refractometer, a Talbot-Moire refractometer, a ray-tracing refractometer, a wavefront analyzer, an aberration detector, and an aberrometer.

3. The method of claim 1, wherein the OCT imaging system comprises one of a time-domain, a frequency-domain, a swept frequency, and a Fourier Domain Mode Locking OCT imaging system.

4. The method of claim 1, wherein the refractometer and the OCT imaging system are mounted on a microscope.

5. The method of claim 1, wherein refractometer and the OCT imaging system are integrated with a microscope.

6. The method of claim 1, wherein executing the optical ray tracing software to determine the refractive characteristics of the eye comprises determining one or more parameters of an eye-model using both the OCT image data and the refractive mapping data.

7. The method of claim 6, wherein:
   the eye-model is one of an Emsley model, a Greivenkamp model, a Gullstrand model, a Helmholtz-Laurence model and a Liou-Brennan model; and
   the one or more parameters of the eye-model include at least one of a spherical parameter, a cylinder parameter, and an orientation angle of an astigmatism of the eye.

8. The method of claim 6, wherein the one or more parameters of the eye-model are determined using both the OCT image data and the refractive mapping data after a natural lens of the eye has been removed; and
   further comprising outputting corrective biometry information to a display when the determined eye-model parameters are different from pre-operatively determined eye-model parameters.

9. The method of claim 6, wherein the one or more parameters of the eye-model are determined using both the OCT image data and the refractive mapping data after a relaxing incision has been created in an ophthalmic tissue; and further comprising outputting corrective biometry information to a display when the determined eye-model parameters are different from pre-operatively determined eye-model parameters.

10. The method of claim 6: wherein the one or more parameters of the eye-model are determined using both the OCT image data and the refractive mapping data after an IOL lens has been inserted into a capsule of the eye; and
further comprising outputting, to a display, biometry information to guide an adjustment of at least one of a centration and a toric orientation of the inserted IOL.

11. The method of claim 6, further comprising selecting from a database of available Intra Ocular Lenses (IOLs), based on the determined parameters of the eye-model, optical characteristics of an IOL to achieve an optical correction of the eye.

12. The method of claim 11, wherein the optical correction is related to at least one of the following characteristics of the eye: a spherical refractive error, a cylindrical refractive error, an astigmatism value, an astigmatism angle, an optical power, a higher order aberration, a coma, a Zernike coefficient, a centration, and a tilt.

13. The method of claim 11, further comprising:
determining, by the processor, at least one of a recommended IOL optical power, a value and orientation of an astigmatism of a toric IOL, a multifocal characteristic, and a position of an Intra Ocular Lens (IOL) in a capsule of the eye to achieve the desired optical correction of the eye.

14. A system for determining refractive characteristics of an eye, comprising:
an Optical Coherence Tomographic (OCT) imaging system configured to generate OCT image data of an imaged region of the eye;
a refractometer configured to generate refractive mapping data of the imaged region;
an optical analytic software program executable by a processor, the optical analytic software program configured to:
receive the OCT image data and the refractive mapping data;
register the OCT image data and the refractive mapping data;
combine the OCT image data and refractive mapping data; and
execute optical ray tracing software to determine the refractive characteristics of the eye based on the combined OCT image data and refractive mapping data.

15. The system of claim 14, further comprising:
a surgical microscope, configured to provide a visual image of the imaged region of the eye, and
a display, configured to display biometric information indicating the determined refractive characteristics of the eye.

16. The system of claim 14, wherein the refractometer comprises at least one of a Shack-Hartmann refractometer, a Talbot-Moire refractometer, a ray-tracing refractometer, a wavefront analyzer, an aberration detector, and an aberrometer.

17. The system of claim 14, wherein the OCT imaging system comprises one of a time-domain, a frequency-domain, a swept frequency, and a Fourier Domain Mode Locking OCT imaging system.

18. The system of claim 14, wherein the refractometer or the OCT imaging system is mounted on a microscope.

19. The method of claim 14, wherein the refractometer or the OCT imaging system is integrated with a microscope.

20. The system of claim 14, wherein the optical analytic software program is further configured to determine one or more parameters of an eye-model using both the OCT image data and the refractive mapping data.

21. The system of claim 20, wherein:
the eye-model is one of an Emsley model, a Greivenkamp model, a Gullstrand model, a Helmholtz-Laurence model and a Liou-Brennan model; and
the one or more parameters of the eye-model include at least one of a spherical parameter, a cylinder parameter, and an orientation angle of an astigmatism of the eye.

22. The system of claim 20, wherein the one or more parameters of the eye-model are determined by the optical analytic software program after a natural lens of the eye has been removed; and
the optical analytic software program is further configured to output corrective biometry information to a display when the determined eye-model parameters are different from pre-operatively determined eye-model parameters.

23. The system of claim 20, wherein the one or more parameters of the eye-model are determined by the optical analytic software program after a relaxing incision has been created in an ophthalmic tissue; and
the optical analytic software program is further configured to ouput corrective biometry information to a display when the determined eye-model parameters are different from pre-operatively determined eye-model parameters.

24. The system of claim 20, wherein the one or more parameters of the eye-model are determined by the optical analytic software after an IOL lens has been inserted into a capsule of the eye; and
the optical analytic software program is further configured to output, to a display, biometry information to guide an adjustment of at least one of a centration and a toric orientation of the inserted IOL.

25. The system of claim 20, wherein the optical analytic software program is further configured to select, based on the determined parameters of the eye-model, optical characteristics of an Intra Ocular Lenses (IOL) to achieve an optical correction of the eye.

26. The system of claim 25, wherein the optical correction is related to at least one of the following characteristics of the eye: a spherical refractive error, a cylindrical refractive error, an astigmatism value, an astigmatism angle, an optical power, a higher order aberration, a coma, a Zernike coefficient, a centration, and a tilt.

27. The system of claim 25, wherein the optical analytic software program is further configured to determine at least one of a recommended IOL optical power, a value and orientation of an astigmatism of a toric IOL, a multifocal characteristic, and a position of an IOL in a capsule of the eye to achieve the optical correction of the eye.

28. An intra-operative biometer system, comprising:
an Optical Coherence Tomographic (OCT) imaging system configured to generate OCT image data of an imaged region of an eye during an ophthalmic operation;
a refractometer configured to generate refractive mapping data of the imaged region during the ophthalmic operation;
a processor configured to execute an optical analytic software program during the ophthalmic operation to:

receive the OCT image data and the refractive mapping data;
register the OCT image data and the refractive mapping data;
combine the OCT image data and refractive mapping data; and
execute optical ray tracing software during a surgical procedure to determine one or more parameters of an eye-model based on the combined OCT image data and refractive mapping data;
select, based on the determined parameters of the eye-model, characteristics of an Intra Ocular Lenses (IOL) to achieve an optical correction of the eye; and
determine at least one of a recommended IOL optical power, a value and orientation of an astigmatism of a toric IOL, a multifocal characteristic, and a position of an IOL in a capsule of the eye to achieve the optical correction of the eye.

* * * * *